United States Patent [19]

Houminer et al.

[11] Patent Number: 5,199,450
[45] Date of Patent: Apr. 6, 1993

[54] SMOKING COMPOSITIONS CONTAINING A TARTRATE SALT FLAVORANT-RELEASE ADDITIVE

[75] Inventors: Yoram Houminer, Richmond; John D. Naworal, Midlothian, both of Va.

[73] Assignees: Philip Morris Incorporated, New York, N.Y.; Philip Morris Products Inc., Richmond, Va.

[21] Appl. No.: 660,932

[22] Filed: Feb. 26, 1991

[51] Int. Cl.$^5$ .............................................. A24B 15/30
[52] U.S. Cl. ..................................... 131/276; 131/274
[58] Field of Search ............................... 131/276, 274

[56] References Cited

PUBLICATIONS

"Tobacco Flavoring for Smoking Products" by Leffingwell et al. Publ. by R. J. Reynolds in 1972, pp. 19, 27 and 63.

*Primary Examiner*—V. Millin
*Assistant Examiner*—J. Doyle
*Attorney, Agent, or Firm*—James E. Schardt

[57] ABSTRACT

This invention provides smoking compositions which contain a novel tartrate salt flavorant-release additive, such as an acetal derivative corresponding to the formula:

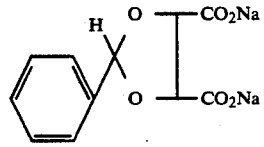

Under cigarette smoking conditions, a combustible filler and/or paper wrapper additive as illustrated above pyrolyzes and releases benzaldehyde flavorant as a volatile component of the cigarette smoke.

20 Claims, No Drawings

SMOKING COMPOSITIONS CONTAINING A TARTRATE SALT FLAVORANT-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,914,451; 3,915,175; 3,920,027; 3,924,644; 3,937,228; 3,943,943; 3,586,387; 3,379,754; and the like.

J. C. Leffingwell et al "Tobacco Flavoring For Smoking Products" (R. J. Reynolds publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as l-menthyl linalool carbonate. Under smoking conditions pyrolysis of the carbonate ester releases menthol which flavors the mainstream smoke.

U.S. Pat. Nos. 3,332,428 and 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,177,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe $\beta$-hydroxyesters which as additives in smoking compositions pyrolyze into volatile aldehyde and ester flavorants under smoking conditions.

U.S. Pat. Nos. 4,473,085 and 4,607,118 describe $\beta$-hydroxyesters which as additives in smoking compositions pyrolyze into volatile ketone and ester flavorants under smoking conditions.

Of general interest with respect to the present invention is the proposed utilization of carboxylate metal salts as additives in the combustible filler of smoking compositions to modify the composition and properties of generated smoke, such as described in U.S. Pat. Nos. 3,924,642 and 4,489,739.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel acetals and ketals of tartrate salt compounds which are adapted to be incorporated into cigarette filler and/or paper wrapper components, and which under normal smoking conditions release a volatile aldehyde or ketone flavorant into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

$$\begin{array}{c} R \\ \diagdown \\ R^1 \end{array} \!\!\! X \!\!\! \begin{array}{c} O - \!\!\!\!\!\!\!\!\!\!\!\!\! - CO_2M \\ \\ O - \!\!\!\!\!\!\!\!\!\!\!\!\! - CO_2M \end{array} \qquad I$$

where R is hydrogen or a $C_1$–$C_4$ alkyl substituent; $R^1$ is a $C_1$–$C_{12}$ hydrocarbyl substituent; and M is an alkali or alkaline earth metal.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

$$\begin{array}{c} R \\ \diagdown \\ R^1 \end{array} \!\!\! X \!\!\! \begin{array}{c} O - \!\!\!\!\!\!\!\!\!\!\!\!\! - CO_2M \\ \\ O - \!\!\!\!\!\!\!\!\!\!\!\!\! - CO_2M \end{array}$$

where R is hydrogen or a $C_1$–$C_4$ alkyl substituent; $R^1$ is a $C_1$–$C_{12}$ hydrocarbyl substituent; and M is an alkali or alkaline earth metal.

Illustrative of $C_1$–$C_4$ alkyl substituents in the above represented flavorant-release additive formula I are methyl, ethyl, propyl, 2-propyl, butyl, 2-butyl and isobutyl groups.

Illustrative of $C_1$–$C_{12}$ hydrocarbyl substituents in formula I are methyl, ethyl, butyl, hexyl, ethenyl, propenyl, phenyl, benzyl, phenylethyl, methoxyphenyl, cinnamyl, and the like.

Illustrative of M substituents in the above represented formula I are alkali metal and alkaline earth metals such as sodium, potassium, magnesium and calcium.

A cigarette smoking product in accordance with the present invention typically contains between about 0.01-5 weight percent of flavorant-release additive in the paper wrapper, based on the weight of combustible filler.

In a further embodiment an invention cigarette product contains between about 0.01-5 weight percent of flavorant-release additive in the paper wrapper, and contains between about 0.0001-5 weight percent of a flavorant-release additive in the combustible filler, based on the weight of filler.

A present invention flavorant-release additive in accordance with formula I which is incorporated in smoking compositions as described above is a low volatility compound which under normal smoking conditions pyrolyzes and releases a volatile aldehyde or ketone constituent which enhances the flavor and aroma of low delivery cigarettes:

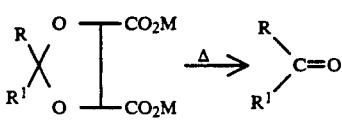

As demonstrated in Example V, a present invention formula I compound is an efficient flavorant-releasing agent in comparison with the corresponding diester derivative.

An important advantage of a present invention formula I flavorant-release compound is an excellent stability property when utilized as a cigarette paper additive and the paper is exposed to variable conditions of light and moisture. Cigarette paper treated with a present invention flavorant-release additive does not discolor under light and moisture exposure conditions due to decomposition of the additive.

An invention formula I tartrate salt is slightly basic since it derives from a strong base and a weak acid. The inherent buffer property provides stability under humidity conditions when a tartrate salt is used as a cigarette constituent.

Preparation of Tartrate Salt Compounds

In another embodiment this invention provides a process for producing an acetal or ketal of a tartrate salt which comprises (1) forming an aqueous alcoholic solution of a tartrate diester corresponding to the formula:

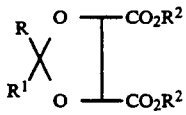

where R is hydrogen or a $C_1-C_4$ alkyl substituent, $R^1$ is a $C_1-C_{12}$ hydrocarbyl substituent, and $R^2$ is a $C_1-C_6$ alkyl substituent; and (2) treating the solution with at least a molar equivalent weight of an alkali or alkaline earth metal hydroxide to hydrolyze the tartrate diester to a tartrate salt corresponding to the formula:

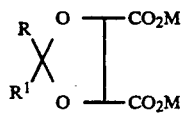

where R is hydrogen or a $C_1-C_4$ alkyl substituent; $R^1$ is a $C_1-C_{12}$ hydrocarbyl substituent; and M is an alkali or alkaline earth metal.

The tartrate diester compound in step(1) can be prepared by the reaction of dialkyl tartrate with a corresponding aldehyde or ketone in the presence of trialkyl orthoformate and an acid catalyst such as p-toluenesulfonic acid:

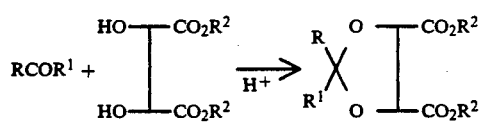

The step(2) hydrolysis reaction can be conducted in an aqueous solution of a water-miscible alcohol such as methanol, ethanol or propanol, at a temperature between about 0°-60° C. for a reaction period between about 0.5-24 hours until the hydrolysis reaction is completed.

In a preferred embodiment the step(2) hydrolysis reaction is conducted in an aqueous ethanol solution at room temperature with sodium or potassium hydroxide reagent in slight excess to the tartrate diester. The process yields an aqueous alcoholic solution of an invention formula I tartrate salt which can be utilized directly for incorporation of the tartrate salt in combustible filler and/or cigarette paper wrappers as a flavorant-release additive.

Preparation Of Tobacco Compositions

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant-release additive corresponding to formula I as defined above.

The invention flavorant-release additive can be incorporated into the tobacco or tobacco substitute in accordance with methods known and used in the art. Preferably the flavorant-release additive is contained in a solvent such as aqueous alcohol and then sprayed or injected into the tobacco and/or tobacco substitute matrix. Such method ensures an even distribution of the flavorant-release additive throughout the filler, and thereby facilitates the production of a more uniform smoking composition. Alternatively, the additive may be incorporated as part of a concentrated tobacco extract which is applied to a fibrous tobacco web as in the manufacture of reconstituted tobacco. Another suitable procedure is to incorporate the additive in tobacco or tobacco substitute filler in a concentration between about 0.5-5 weight percent, based on the weight of filler, and then subsequently to blend the treated filler with filler which does not contain flavorant-release additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

As previously described hereinabove, an invention flavorant-release additive also can be incorporated in the paper wrapper of cigarette products, for the purpose of enhancing the aroma of cigarette sidestream smoke under smoking conditions.

The following Examples are further illustrative of the present invention. The specific ingredients and processing parameters are presented as being typical, and various modifications can be derived in view of the foregoing disclosure within the scope of the invention.

EXAMPLE I (4R,5R)-Diethyl 2-(1-benzylideneheptyl)-1,3-dioxolane-4,5-dicarboxylate

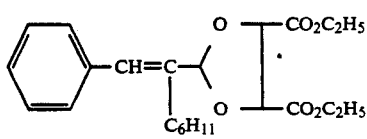

A solution of α-hexylcinnamaldehyde (62.19 g, 0.288 mole), triethyl orthoformate (42.61 g, 0.288 mole), diethyl L-tartrate (51.5 g, 0.25 mole) in toluene (180 ml) containing p-toluene sulfonic acid (0.8 g) was refluxed for 1 hour. About 100 ml of ethanol-toluene mixture was distilled over a period of 2 hours, and after cooling the remaining solvent was removed on a rotary evaporator. The residue was dissolved in toluene (200 ml) and the solution was washed with aqueous $NaHCO_3$ and then with water. The solution was dried over $Na_2SO_4$, and the solvent was evaporated under reduced pressure to provide a brown liquid (110.1 g).

The crude material was distilled in a Kugelrohr apparatus under vacuum (0.05 mm Hg) and a fraction boiling at 150°–160° C. was collected (92.4 g; 91% yield). NMR confirmed the structure of the title compound and indicated that the material was a 2:1 mixture of the (E)- and (Z)-isomers. MS confirmed both structure and molecular weight.

Anal. calc. for $C_{23}H_{32}O_6$: C,68.29; H,7.97. Found: C,68.44; H.7.96

EXAMPLE II (4R,5R)-Dimethyl 2-(1-benzylideneheptyl)-1,3-dioxolane-4,5-dicarboxylate

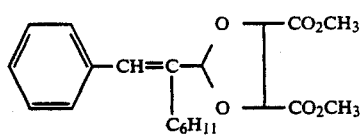

The reaction of α-hexylcinnamaldehyde (13.0 g, 0.06 mole), with dimethyl L-tartrate (8.9 g, 0.05 mole) in toluene (50 ml) in the presence of trimethyl orthoformate (6.37 g, 0.06 mole), and p-toluene sulphonic acid (0.2 g) was carried out in the manner of Example I. The methanol formed in the reaction was removed by distillation. The Example I product recovery procedure gave an oily residue (21.8 g). The oil solidified after 24 hours, and crystallization from hexane afforded needles. The solid was recovered by filtration, and washed with cold hexane to yield 8.1 g of white needles (43% yield), mp 49°–51° C. NMR confirmed the structure of the title compound and indicated that the material was pure (E)-isomer.

MS confirmed both structure and molecular weight.

Anal. calc. for $C_{21}H_{28}O_6$: C,67 00; H,7.50. Found: C,66.90; H,7.57

The mother liquor from the above crystallization was concentrated to yield an oil which partially solidified on standing. NMR of this crude material indicated that it was about a 1:1 mixture of the corresponding (E)- and (Z)- isomers.

EXAMPLE III (4R,5R)-Disodium 2-phenyl-1,3-dioxolane-4,5-dicarboxylate

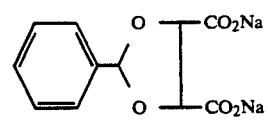

To a stirred solution of (4R,5R)-dimethyl 2-phenyl-1,3-dioxolane-4,5-dicarboxylate (2.66 g, 0.01 mole) (Aldrich) in methanol (90 ml) at room temperature was added a solution of sodium hydroxide (0.84 g, 0.021 mole) in water (10 ml). The mixture was stirred at room temperature for an additional 3 hours, then the solvent was evaporated at 45° C. under reduced pressure. Absolute ethanol was added and the solvent was evaporated to provide 2.9 g of a hygroscopic white powder. The material was washed with ethyl acetate and dried under vacuum. NMR confirmed the structure of the title compound.

EXAMPLE IV (4R,5R)-Disodium 2-(1-benzylideneheptyl)-1,3-dioxolane-4,5-dicarboxylate

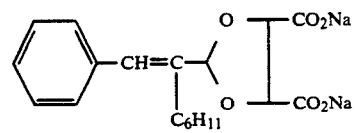

Procedure A

To a stirred solution of the dimethyl ester (37.65 g, 0.1 mole) of Example II in methanol (500 ml) at room temperature was added a solution of sodium hydroxide (8.1 g, 0.20025 mole) in water (80 ml). The mixture was stirred at room temperature for an additional 2 hours. The clear solution had a final pH of 9. Most of the solvent was removed at 45° C. on the rotary evaporator under vacuum to provide a hygroscopic white solid (36.5 g). To remove residual water from the solid, 500 ml of absolute ethanol was added and the solvent was evaporated under reduced pressure. The drying procedure was repeated twice to yield a fine powder, mp 245°–250° C. (decomp.) NMR confirmed the structure of title compound. FAB-MS indicated a mass corresponding to the formula $C_{19}H_{22}Na_2$.

Anal. calc. for $C_{19}H_{22}O_6 \cdot H_2O$: C,55.61; H,5.89. Found: C,55.75; H,5.67

A slight excess of base is required to ensure complete hydrolysis of the ester (pH of 8–9). If the final pH of the solution is between 7–7.5, some decomposition of the acetal group occurs during the course of the reaction and during workup.

Procedure B

A solution of NOH (2.05 g, 0.051 mole) in water (50 ml) is added to a solution of the Example I diester (20.23 g, 0.05 mole) in 95% ethanol (950 ml) at room temperature with stirring. The mixture is stirred at room temperature for 2 hours, and the final pH of the solution is 9.

The product solution is suitable for application to filler or wrapper for purposes of cigarette manufacture.

EXAMPLE V

Comparative Pyrolysis Experiments

A sample of about 0.05 mg of each of the compounds listed below was pyrolyzed in a ceramic boat at 300° C., in a quartz tube furnace under helium atmosphere. The analysis was carried out using a Siemans Sichromat 2 GC attached to a Finnigan Mat SSQ70 MS instrument. The volatile pyrolyzate was condensed at −50° C. in a 3 inch section of a 30 meter DB-5 fused silica capillary column. This section of column was rapidly heated to the oven temperature after pyrolysis of the sample. The oven temperature, initially at 0° C. for 4 minutes, was programmed at 7° C. per minute to 280° C. Three minutes after the onset of pyrolysis, spectra covering a range of m/z 33 to 500 were obtained by scanning every second.

| Example compound | Released aldehyde % | Unreacted starting material % |
| --- | --- | --- |
| I (diester) | 3.6 | 96.4 |
| II (diester) | 1.0 | 98.8 |
| (4R,5R)-Dimethyl 2-phenyl-1,3-dioxolane-4,5-dicarboxylate | 1.8 | 98.2 |
| III (salt) | 90.1 | (a) |
| IV (salt) | 89.8 | (a) |

(a) No detectable starting material was observed for invention compounds.

EXAMPLE VI

A 2% solution of the invention disodium salt of Example IV in 95% ethanol was applied to the paper wrapper of cigarettes (about 0.3 mg per cigarette) and the cigarettes were smoked and evaluated by an experienced smoking panel. Compared to untreated control cigarettes, the treated cigarettes exhibit pleasant floral-green, herbal-spicy aromas in the sidestream smoke, without a significant change in the mainstream smoke flavor. The sidestream smoke was also reported to be less irritating compared to the control.

What is claimed is:

1. A smoking composition comprising an admixture of
   (1) combustible filler selected from natural tobacco, reconstituted tobacco and tobacco substitutes, and
   (2) between about 0.0001-5 weight percent, based on the total weight of filler, of a flavorant-release additive corresponding to the formula:

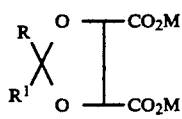

where R is hydrogen or a $C_1$-$C_4$ alkyl substituent; $R^1$ is a $C_1$-$C_{12}$ hydrocarbyl substituent; and M is an alkali or alkaline earth metal.

2. A smoking composition in accordance with claim 1 wherein the flavorant-release additive is an acetal of benzaldehyde.

3. A smoking composition in accordance with claim 1 wherein the flavorant-release additive is an acetal of α-hexylcinnamaldehyde.

4. A smoking composition in accordance with claim 1 wherein M in the additive formula is sodium, potassium, magnesium or calcium.

5. A cigarette smoking product comprising
   (1) a combustible filler selected from natural tobacco, reconstituted tobacco and tobacco substitutes, and
   (2) a paper wrapper which has incorporated therein a flavorant-release additive corresponding to the formula:

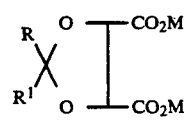

where R is hydrogen or a $C_1$-$C_4$ alkyl substituent; $R^1$ is a $C_1$-$C_{12}$ hydrocarbyl substituent; and M is an alkali or alkaline earth metal.

6. A cigarette smoking product in accordance with claim 5 wherein the paper wrapper contains between about 0.01-5 weight percent of flavorant-release additive.

7. A cigarette smoking product in accordance with claim 5 wherein the flavorant-release additive is an acetal of benzaldehyde.

8. A cigarette smoking product in accordance with claim 5 wherein the flavorant-release additive is an acetal of α-hexylcinnamaldehyde.

9. A cigarette smoking product in accordance with claim 5 wherein M in the additive formula is sodium, potassium, magnesium or calcium.

10. A cigarette smoking product in accordance with claim 5 wherein the combustible filler contains between about 0.0001-5 weight percent, based on the weight of filler, of a flavorant-release additive corresponding to the formula:

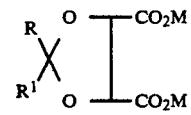

where R is hydrogen or a $C_1$-$C_4$ alkyl substituent; $R^1$ is a $C_1$-$C_{12}$ hydrocarbyl substituent; and M is an alkali or alkaline earth metal.

11. A cigarette smoking product in accordance with claim 10 wherein the flavorant-release additive in the combustible filler is an acetal of benzaldehyde.

12. A cigarette smoking product in accordance with claim 10 wherein the flavorant-release additive in the combustible filler is an acetal of α-hexylcinnamaldehyde.

13. A cigarette smoking product in accordance with claim 10 wherein M in the additive formula is sodium, potassium, magnesium or calcium.

14. A tartrate acetal or ketal corresponding to the formula:

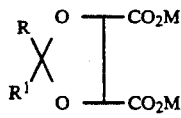

where R is hydrogen or a $C_1$–$C_4$ alkyl substituent; $R^1$ is an aromatic hydrocarbyl substituent; and M is an alkali or alkaline earth metal.

15. A tartrate in accordance with claim 14 which is an acetal of benzaldehyde.

16. A tartrate in accordance with claim 14 which is an acetal of α-hexylcinnamaldehyde.

17. A tartrate in accordance with claim 14 wherein M in the formula is sodium, potassium, magnesium or calcium.

18. An aqueous alcoholic solution of a tartrate acetal or ketal compound corresponding to the formula:

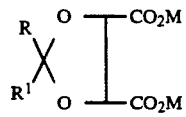

where R is hydrogen or an aromatic alkyl substituent; $R^1$ is a $C_1$–$C_{12}$ hydrocarbyl substituent; and M is an alkali or alkaline earth metal.

19. An aqueous alcoholic solution in accordance with claim 18 wherein the compound is a tartrate acetal of benzaldehyde.

20. An aqueous alcoholic solution in accordance with claim 18 wherein the compound is a tartrate acetal of α-hexylcinnamaldehyde.

* * * * *